US010793508B2

(12) United States Patent
Essaddam et al.

(10) Patent No.: US 10,793,508 B2
(45) Date of Patent: *Oct. 6, 2020

(54) TEREPHTHALIC ACID ESTERS FORMATION

(71) Applicant: 9449710 CANADA INC., Terrebonne (CA)

(72) Inventors: Adel Essaddam, Sherbrooke (CA); Fares Essaddam, Sainte-Therese (CA)

(73) Assignee: 9449710 CANADA INC., Terrebonne (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/259,980

(22) Filed: Jan. 28, 2019

(65) Prior Publication Data

US 2019/0256450 A1 Aug. 22, 2019

Related U.S. Application Data

(63) Continuation of application No. 15/706,484, filed on Sep. 15, 2017, now Pat. No. 10,252,976.

(51) Int. Cl.
| | | |
|---|---|---|
| *C07C 69/82* | (2006.01) | |
| *C08L 101/00* | (2006.01) | |
| *C07C 29/09* | (2006.01) | |
| *C07C 29/128* | (2006.01) | |
| *C07C 31/20* | (2006.01) | |
| *C07C 51/09* | (2006.01) | |
| *C07C 67/08* | (2006.01) | |
| *C08F 8/50* | (2006.01) | |
| *C08J 7/02* | (2006.01) | |
| *C08J 11/24* | (2006.01) | |
| *C08J 11/26* | (2006.01) | |
| *C08K 5/05* | (2006.01) | |
| *C08L 67/03* | (2006.01) | |

(52) U.S. Cl.
CPC ............ *C07C 69/82* (2013.01); *C07C 29/095* (2013.01); *C07C 29/1285* (2013.01); *C07C 31/202* (2013.01); *C07C 51/09* (2013.01); *C07C 67/08* (2013.01); *C08F 8/50* (2013.01); *C08J 7/02* (2013.01); *C08J 11/24* (2013.01); *C08J 11/26* (2013.01); *C08K 5/05* (2013.01); *C08L 67/03* (2013.01); *C08L 101/00* (2013.01); *C08J 2367/03* (2013.01)

(58) Field of Classification Search
None
See application file for complete search history.

(56) References Cited

U.S. PATENT DOCUMENTS

| | | | |
|---|---|---|---|
| 3,219,622 A | 11/1965 | Luciano et al. |
| 3,501,420 A | 3/1970 | Stevenson et al. |
| 3,520,940 A | 7/1970 | Smith, Jr. et al. |
| 4,163,860 A | 8/1979 | Delattre et al. |
| 4,355,175 A | 10/1982 | Pusztaszeri |
| 5,045,122 A | 9/1991 | Tindall et al. |
| 5,051,528 A | 9/1991 | Naujokas et al. |
| 5,236,959 A | 8/1993 | Oakley et al. |
| 5,328,982 A | 7/1994 | Tindall et al. |
| 5,386,055 A | 1/1995 | Lee et al. |
| 5,668,186 A | 9/1997 | Brunelle et al. |
| 6,528,546 B2 | 3/2003 | Lee et al. |
| 6,670,503 B2 | 12/2003 | Broccatelli |
| 6,706,843 B1 | 3/2004 | Ishihara et al. |
| 6,720,448 B2 | 4/2004 | Broccatelli |
| 6,911,546 B2 | 6/2005 | Hedrick et al. |
| 6,916,936 B2 | 7/2005 | Hedrick et al. |
| 7,053,221 B2 | 5/2006 | Hedrick et al. |
| 7,462,649 B2 | 12/2008 | Nakao et al. |
| 7,544,800 B2 | 6/2009 | Hedrick et al. |
| 7,750,057 B2 | 7/2010 | Ogasawara |
| 8,309,618 B2 | 11/2012 | Hedrick et al. |
| 8,492,504 B2 | 7/2013 | Hedrick et al. |
| 8,513,379 B2 | 8/2013 | Matsumura |
| 9,550,713 B1 | 1/2017 | Essaddam |
| 1,008,713 A1 | 10/2018 | Essaddam |
| 1,025,297 A1 | 4/2019 | Essaddam et al. |
| 2008/0242751 A1 | 10/2008 | Kurian et al. |
| 2009/0032015 A1 | 2/2009 | Myllymaki et al. |
| 2009/0171113 A1 | 7/2009 | Anderson et al. |
| 2009/0318579 A1 | 12/2009 | Ikenaga |
| 2011/0004014 A1 | 1/2011 | Hedrick et al. |
| 2013/0345453 A1 | 12/2013 | Sipos et al. |
| 2017/0113995 A1 | 4/2017 | Mastrangelo et al. |
| 2018/0370984 A1 | 12/2018 | Essaddam |

(Continued)

FOREIGN PATENT DOCUMENTS

| | | |
|---|---|---|
| CA | 2069500 A1 | 6/1991 |
| CN | 1585798 A | 2/2005 |
| CN | 101628909 A | 1/2010 |

(Continued)

OTHER PUBLICATIONS

ACS. Common Organic Solvents: Table of Properties. downloaded from https://www.organicdivision.org/orig/organic_solvents.html on Apr. 4, 2018, p. 1-2).
Adeakin et al. Polymer—Solvent Relation: Swelling and Fibre Morphology. IOSR-JPTE 4(2):27-28 (2017).
Balcerzyk. Behavior of swollen poly(ethylene terephthalate) on the action of alkali solutions. Kolloid-Z.u.Z. Polymere 251:776-778 (1973).
Falbe. Alcohols, Aliphatic—Ullmann's Encyclopedia of Industrial Chemistry. Downloaded from https://doi.org/10.1002/14356007.a01_279.pub2, first published Jan. 15, 2013, p. 1-26.
Feghali et al. Room Temperature Organocatalyzed Reductive Depolymerization of Waste Polyethers Polyesters and Polycarbonates. ChemSusChem. 8(6):980-984 (2015).

(Continued)

*Primary Examiner* — Amy C Bonaparte
(74) *Attorney, Agent, or Firm* — Wilson Sonsini Goodrich & Rosati

(57) ABSTRACT

The present disclosure relates to the formation of terephthalate esters. The present invention also relates to the depolymerization of polyethylene terephthalate (PET) or poly(ethylene glycol-co-1,4-cyclohexanedimethanol terephthalate) and the recovery of terephthalate esters.

10 Claims, No Drawings

(56) References Cited

U.S. PATENT DOCUMENTS

2019/0390035 A1    12/2019    Essaddam et al.

FOREIGN PATENT DOCUMENTS

| | | | |
|---|---|---|---|
| CN | 102746460 | A | 10/2012 |
| CN | 104327254 | A | 2/2015 |
| CN | 105601507 | A | 5/2016 |
| EP | 1710226 | A1 | 10/2006 |
| FR | 2335490 | A1 | 7/1977 |
| GB | 784248 | A | 10/1957 |
| JP | 2001192492 | A | 7/2001 |
| JP | 2001261707 | A | 9/2001 |
| JP | 2006045371 | A | 2/2006 |
| JP | 2006052173 | A | 2/2006 |
| JP | 4365592 | B2 | 11/2009 |
| JP | 4575074 | B2 | 11/2010 |
| JP | 2014070132 | A | 4/2014 |
| WO | WO-9527753 | A1 | 10/1995 |
| WO | WO-9724310 | A1 | 7/1997 |
| WO | WO-9746611 | A1 | 12/1997 |
| WO | WO-9803459 | A1 | 1/1998 |
| WO | WO-0047659 | A1 | 8/2000 |
| WO | WO-0158982 | A1 | 8/2001 |
| WO | WO-0218471 | A2 | 3/2002 |
| WO | WO-0238276 | A1 | 5/2002 |
| WO | WO-2005003217 | A1 | 1/2005 |
| WO | WO-2006021063 | A1 | 3/2006 |
| WO | WO-2007076384 | A2 | 7/2007 |
| WO | WO-2007096326 | A1 | 8/2007 |
| WO | WO-2007113872 | A1 | 10/2007 |
| WO | WO-2007148353 | A1 | 12/2007 |
| WO | WO-2008007384 | A1 | 1/2008 |
| WO | WO-2017007965 | A1 | 1/2017 |
| WO | WO-2019051597 | A1 | 3/2019 |
| WO | WO-2020002999 | A2 | 1/2020 |

OTHER PUBLICATIONS

Haga. Anomalous Swelling of Poly(ethylene terephthalate) fiber in organic solvents. Journal of Polymer Science, Polymer Letters Edition 20:629-634 (1982).

Haga. Case II swelling of poly(ethylene terephthalate) in organic solvents. Journal of Applied Polymer Science 26(8):2649-2655 (1981).

Kurokawa et al. Methanolysis of polyethylene terephthalate (PET) in the presence of aluminium tiisopropoxide catalyst to form dimethyl terephthalate and ethylene glycol. Polymer Degradation and Stability 79(3):529-533 (2003).

Mishra et al. Kinetic and thermodynamic study of methanolysis of poly(ethylene terephthalate) waste powder. Polym Int 52:337-342 (2003).

Namboori et al. Steric effects in the basic hydrolysis of poly(ethylene terephthalate). Journal of Applied Polymer Science 12:1999-2005 (1968).

PCT/CA2018/051135 International Search Report and Written Opinion dated Dec. 4, 2018.

PCT/US2016/041392 International Search Report and Written Opinion dated Nov. 10, 2016.

Ramsden et al. Factors Influencing the Kinetics of the Alkaline Depolymerisation of Poly(ethylene terephthalate) I: The Effect of Solvent. J Chem Tech Biotechnol 67:131-136 (1996).

Sheehan. Terephthalic Acid, Dimethyl Terephthalate, and Isophthalic Acid. Ullmann's Encyclopedia of Industrial Chemistry 36:17-28 (2011).

U.S. Appl. No. 14/795,116 Office Action dated Jun. 2, 2016.

U.S. Appl. No. 15/377,460 Office Action dated Jan. 29, 2018.

U.S. Appl. No. 15/706,484 Office Action dated Apr. 13, 2018.

U.S. Appl. No. 15/706,484 Office Action dated Oct. 15, 2018.

U.S. Appl. No. 16/117,672 Office Action dated May 15, 2019.

Venkatachalam et al. Materials Science "Polyester"—Chapter 4: Degradation and Recyclability of Poly(Ehtylene Terephthalate). Intech 24 pgs. (2012).

Co-pending U.S. Appl. No 16/821,870, filed Mar. 17, 2020.

PCT/IB2019/000816 International Search Report and Written Opinion dated Jan. 3, 2020.

Shukla et al. Glycolysis of polyethylene terephthalate waste fibers. Journal of Applied Polymer Science 98:513-517 (2005).

U.S. Appl. No. 16/450,807 Office Action dated Feb. 20, 2020.

Al-Sabagh et al. Greener routes for recycling of polyethylene terephthalate. Egyptian Journal of Petroleum 25(1):53-64 (2016).

Moshin et al. Sodium Methoxide Catalyzed Depolymerization of Waste Polyethylene Terephthalate Under Microwave Irradiation. Catal. Ind. 10:41-48 (2018).

PCT/IB2020/000216 International Search Report and Written Opinion dated Jun. 25, 2020.

TEREPHTHALIC ACID ESTERS FORMATION

CROSS-REFERENCE TO RELATED APPLICATION

This application is a continuation application which claims the benefit of priority from U.S. patent application Ser. No. 15/706,484, filed Sep. 15, 2017.

FIELD OF THE INVENTION

The present disclosure relates to the formation of ester derivatives from polyesters and more specifically to the formation of terephthalic acid esters from polyethylene terephthalate (PET) or poly(ethylene glycol-co-1,4-cyclohexanedimethanol terephthalate) (PETG). The present disclosure also relates to the formation of dimethyl terephthalate (DMT).

BACKGROUND OF THE INVENTION

The polyethylene terephthalate (PET) bottle resin market has been growing strongly as PET resins have replaced glass in carbonated soft drink, bottled water and food containers.

Dimethyl terephthalate (DMT) is primarily used in the manufacture of polyethylene terephthalate (PET) for fiber, film, container plastics, and specialty plastics applications.

The largest polyester sector is the fibers market where it is used to make clothes, home textiles such as sheets and curtains, carpets and rugs, and industrial products such as tire cord, seat belts, hoses and ropes. PET film is utilized in electrical applications such as dielectric metal foil capacitors and for food packaging.

The growth in polyester has not been converted into DMT demand. For most grades of polyester used in textiles and food and beverage containers, it is more economical to use purified terephthalic acid rather than DMT.

SUMMARY OF THE INVENTION

Disclosed herein is a process for the transformation of a polyester selected from polyethylene terephthalate and poly(ethylene glycol-co-1,4-cyclohexanedimethanol terephthalate) into a terephthalate of Formula (I):

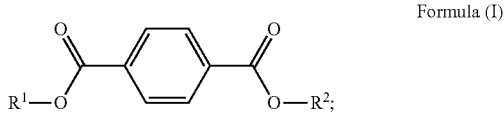

Formula (I)

wherein $R^1$ and $R^2$ are independently selected from hydrogen, $C_1$-$C_6$ alkyl, $C_1$-$C_6$ haloalkyl, $C_1$-$C_6$ hydroxyalkyl, optionally substituted $C_3$-$C_8$ cycloalkyl, optionally substituted ($C_1$-$C_6$ alkyl)($C_3$-$C_8$ cycloalkyl), optionally substituted aryl, and optionally substituted ($C_1$-$C_6$ alkyl)(aryl); provided that one of $R^1$ or $R^2$ is not hydrogen; the process comprising admixing the polyester with a mixture comprising:
  (a) a solvent for swelling the polyester;
  (b) an alcoholic solvent; and
  (c) a sub-stoichiometric amount of an alkoxide.

In some embodiments, $R^1$ or $R^2$ is methyl.

In some embodiments, the alcoholic solvent is selected from methanol, ethanol, n-propanol, isopropanol, t-butanol, ethylene glycol, glycerol, cyclohexane-1,4-diyldimethanol, phenol, benzyl alcohol, and any combinations thereof.

In some embodiments, the alcoholic solvent is methanol.

In some embodiments, the solvent for swelling the polyester is selected from a non polar solvent, a polar aprotic solvent, a polar protic solvent, and any combinations thereof.

In some embodiments, the solvent for swelling the polyester is selected from DMSO, DMF, acetone, a halogenated solvent, n-hexane, nitrobenzene, methanol, benzyl alcohol, benzaldehyde, and any combinations thereof.

In some embodiments, the solvent for swelling the polyester is a halogenated solvent.

In some embodiments, the ratio of solvent for swelling the polyester to alcoholic solvent is between about 0.1:1 and about 2:1 (w:w).

In some embodiments, the ratio of solvent for swelling the polyester to alcoholic solvent is between about 0.5:1 and about 1:1 (w:w).

In some embodiments, the alkoxide is selected from an alkali metal alkoxide, an alkaline earth metal alkoxide, a metal alkoxide, an ammonium alkoxide and any combinations thereof.

In some embodiments, the alkoxide is generated in-situ by addition of an alkali metal, an alkaline earth metal, or a metal to the alcoholic solvent.

In some embodiments, the ratio of polyester to alkoxide is between about 15:1 and about 125:1 (w:w).

In some embodiments, the ratio of polyester to alkoxide is between about 20:1 and about 25:1 (w:w).

In some embodiments, the admixing of the polyester with the solvent for swelling the polyester, the alkoxide, and the alcoholic solvent is performed until an about 80% yield of the terephthalate of Formula (I) is achieved.

In some embodiments, the admixing of the polyester with the solvent for swelling the polyester, the alkoxide, and the alcoholic solvent is performed without external heat.

In some embodiments, the admixing of the polyester with the solvent for swelling the polyester, the alkoxide, and the alcoholic solvent is performed at atmospheric pressure.

Also disclosed herein is a process for the transformation of polyethylene terephthalate into dimethyl terephthalate, comprising admixing the polyethylene terephthalate with a mixture comprising:
  (a) a solvent for swelling the polyethylene terephthalate;
  (b) methanol; and
  (c) a sub-stoichiometric amount of an alkoxide.

In some embodiments, the solvent for swelling the polyethylene terephthalate is selected from a halogenated solvent, DMSO, benzyl alcohol, methanol, and any combinations thereof.

In some embodiments, the ratio of polyethylene terephthalate to alkoxide is between about 20:1 and about 25:1 (w:w).

In some embodiments, the alkoxide is selected from sodium methoxide, potassium ethoxide, aluminium tri-n-propoxide, and tetrabutylammonium methoxide.

In some embodiments, the ratio of solvent for swelling the polyester to methanol is between about 0.5:1 and about 1:1 (w:w).

In some embodiments, the admixing of the polyethylene terephthalate with the solvent for swelling the polyethylene terephthalate, the alkoxide, and the methanol is performed until an about 80% yield of dimethyl terephthalate is achieved.

Also disclosed herein is a reaction mixture comprising:
 (a) a polyester selected from polyethylene terephthalate and poly(ethylene glycol-co-1,4-cyclohexanedimethanol terephthalate);
 (b) a solvent for swelling the polyester;
 (c) an alcoholic solvent; and
 (d) a sub-stoichiometric amount of an alkoxide.

In some embodiments, the alcoholic solvent is selected from methanol, ethanol, n-propanol, isopropanol, t-butanol, ethylene glycol, glycerol, cyclohexane-1,4-diyldimethanol, phenol, benzyl alcohol, and any combinations thereof.

In some embodiments, the solvent for swelling the polyester is selected from a non polar solvent, a polar aprotic solvent, a polar protic solvent, and any combinations thereof.

In some embodiments, the solvent for swelling the polyester is a halogenated solvent and the alcoholic solvent is methanol.

In some embodiments, the ratio of solvent for swelling the polyester to alcoholic solvent is between about 0.5:1 and about 1:1 (w:w).

In some embodiments, the ratio of polyester to alkoxide is between about 15:1 and about 30:1 (w:w).

In some embodiments, the alkoxide is selected from sodium methoxide, potassium ethoxide, aluminium tri-n-propoxide, and tetrabutylammonium methoxide.

In some embodiments, the alkoxide is sodium methoxide.

DETAILED DESCRIPTION OF THE INVENTION

Dimethyl terephthalate (DMT) is used in the production of polyesters, including polyethylene terephthalate (PET), polytrimethylene terephthalate (PTT), and polybutylene terephthalate (PBT). Because DMT is volatile, it is an intermediate in some schemes for the recycling of PET, e.g. from plastic bottles. Hydrogenation of DMT affords the diol 1, 4-cyclohexanedimethanol, which is a useful monomer in the formation of polyester resins.

DMT has been produced in a number of ways. Conventionally and still of commercial value is the direct esterification of terephthalic acid. Alternatively, it is prepared by alternating oxidation and methyl-esterification steps from para-xylene via methyl para-toluate. The method for the production of DMT from para-xylene and methanol consists of four major steps: oxidation, esterification, distillation, and crystallization. A mixture of para-xylene and pare-toluic ester is oxidized with air in the presence of a transition metal catalyst (Co/Mn). The acid mixture resulting from the oxidation is esterified with methanol to produce a mixture of esters. The crude ester mixture is distilled to remove all the heavy boilers and residue produced; the lighter esters are recycled to the oxidation section. The raw DMT is then crystallized to remove DMT isomers, residual acids, and aromatic aldehydes.

An Improvement in DMT production from PET recycling: due to the growing use of PET and PETG in the packaging and fiber (carpet and other textile) industries there is a need for an efficient, low energy, high yielding, and cost effective way to form DMT from PET or PETG.

Polyesters

Described herein is a process for the transformation of a polyester into an ester derivative; the process comprising admixing the polyester with a mixture comprising:
 (a) a solvent for swelling the polyester;
 (b) an alcoholic solvent; and
 (c) a sub-stoichiometric amount of an alkoxide.

In some embodiments, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly (3-hydroxybutyrate-co-3-hydroxyvalerate) (PHBV), polybutylene terephthalate (PBT), polytrimethylene terephthalate (PTT), polyethylene naphthalate (PEN), Vectran®, cutin, and any combinations thereof.

In some embodiments, the polyester is polyethylene terephthalate (PET):

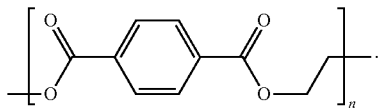

In some embodiments, the polyester is a terephthalic acid/ethylene glycol oligomer.

In some embodiments, the polyester is poly(ethylene glycol-co-1,4-cyclohexanedimethanol terephthalate) (PETG):

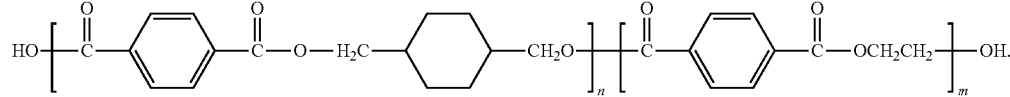

In some embodiments, the polyester is polyglycolide or polyglycolic acid (PGA),

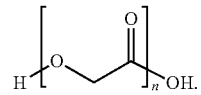

In some embodiments, the polyester is polylactic acid (PLA):

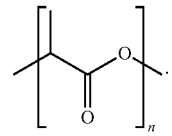

In some embodiments, the polyester is polycaprolactone (PCL):

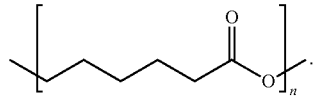

In some embodiments, the polyester is polyhydroxybutyrate (PHB):

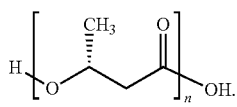

In some embodiments, the polyester is polyethylene adipate (PEA):

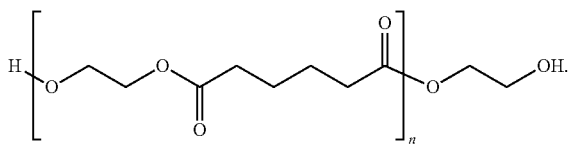

In some embodiments, the polyester is polybutylene succinate (PBS):

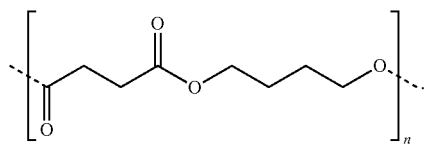

In some embodiments, the polyester is poly(3-hydroxybutyrate-co-3-hydroxyvalerate) (PHBV):

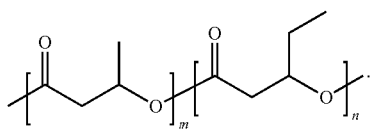

In some embodiments, the polyester is polybutylene terephthalate (PBT):

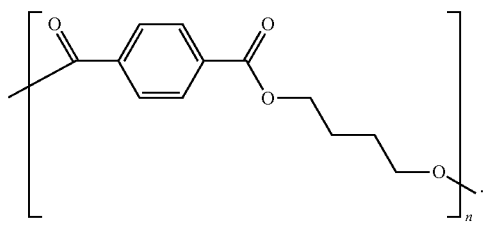

In some embodiments, the polyester is polytrimethylene terephthalate (PTT):

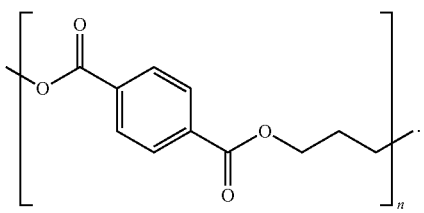

In some embodiments, the polyester is polyethylene naphthalate (PEN):

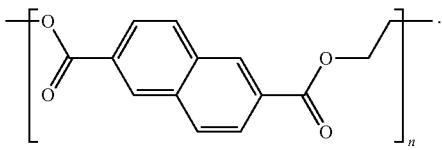

In some embodiments, the polyester is Vectran®:

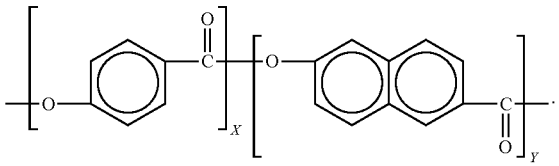

In some embodiments, the polyester is cutin. Cutin is one of two waxy polymers that are the main components of the plant cuticle, which covers all aerial surfaces of plants. Cutin consists of omega hydroxy acids and their derivatives, which are interlinked via ester bonds, forming a polyester polymer. There are two major monomer families of cutin, the C16 and C18 families. The C16 family consists mainly of 16-hydroxy palmitic acid and 9,16- or 10,16-dihydroxypalmitic acid. The C18 family consists mainly of 18-hydroxy oleic acid, 9,10-epoxy-18-hydroxy stearic acid, and 9,10,18-trihydroxystearate. Tomato cutin consists of 16-hydroxy palmitic acid and 10,16-dihydroxypalmitic acid where the 10-isomer is largely dominant. The tomato cutin is a polyester biopolymer interesterificated. The significant proportion of secondary esters (esterification in the C-10 secondary hydroxyl) shows that the polyester structure is significantly branched.

Ester Derivatives

Described herein is a process for the transformation of a polyester into an ester derivative; the process comprising admixing the polyester with a mixture comprising:
(a) a solvent for swelling the polyester;
(b) an alcoholic solvent; and
(c) a sub-stoichiometric amount of an alkoxide.

In some embodiments, the polyester is polyglycolide or polyglycolic acid (PGA) and the ester derivative is a 2-hydroxyacetate derivative. In some embodiments, the ester derivative is methyl 2-hydroxyacetate.

In some embodiments, the polyester is polylactic acid (PLA) and the ester derivative is a 2-hydroxypropanoate derivative. In some embodiments, the ester derivative is methyl 2-hydroxypropanoate.

In some embodiments, the polyester is polycaprolactone (PCL) and the ester derivative is a 6-hydroxyhexanoate derivative. In some embodiments, the ester derivative is a methyl 6-hydroxyhexanoate.

In some embodiments, the polyester is polyhydroxybutyrate (PHB) and the ester derivative is a hydroxybutyrate derivative. In some embodiments, the ester derivative is methyl hydroxybutyrate.

In some embodiments, the polyester is polyethylene adipate (PEA) and the ester derivative is an adipate derivative. In some embodiments, the ester derivative is dimethyl adipate.

In some embodiments, the polyester is polybutylene succinate (PBS) and the ester derivative is a succinate derivative. In some embodiments, the ester derivative is dimethyl succinate.

In some embodiments, the polyester is poly(3-hydroxybutyrate-co-3-hydroxyvalerate) (PHBV) and the ester derivative is a hydroxybutyrate derivative, a hydroxyvalerate derivative, or a combination thereof. In some embodiments, the ester derivative is methyl hydroxybutyrate, methyl hydroxyvalerate, or a combination thereof.

In some embodiments, the polyester is polyethylene naphthalate (PEN) and the ester derivative is a naphthalate derivative. In some embodiments, the ester derivative is dimethyl naphthalate.

In some embodiments, the polyester is vectran and the ester derivative is a naphthoate derivative, a benzoate derivative, or a combination thereof. In some embodiments, the ester derivative is methyl hydroxynaphthoate or methyl hydroxybenzoate.

In some embodiments, the polyester is cutin and the ester derivative is a hydroxypalmitate or a dihydroxypalmitate derivative. In some embodiments, the ester derivative is methyl hydroxypalmitate or methyl dihydroxypalmitate.

In some embodiments, the polyester is polyethylene terephthalate (PET), poly(ethylene glycol-co-1,4-cyclohexanedimethanol terephthalate) (PETG), polytrimethylene terephthalate (PTT), or polybutylene terephthalate (PBT) and the ester derivative is a terephthalate derivative. In some embodiments, the terephthalate derivative is a compound of formula (I):

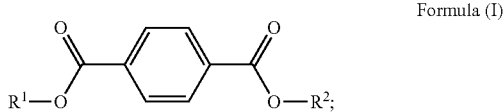

Formula (I)

wherein $R^1$ and $R^2$ are independently selected from hydrogen, $C_1$-$C_6$ alkyl, $C_1$-$C_6$ haloalkyk $C_1$-$C_6$ hydroxyalkyl, optionally substituted $C_3$-$C_8$ cycloalkyl, optionally substituted ($C_1$-$C_6$ alkyl)($C_3$-$C_8$ cycloalkyl), optionally substituted aryl, and optionally substituted ($C_1$-$C_6$ alkyl)(aryl); provided that one of $R^1$ or $R^2$ is not hydrogen.

In some embodiments of a compound of Formula (I), $R^1$ and $R^2$ are independently $C_1$-$C_6$ alkyl or $C_1$-$C_6$ hydroxyalkyl.

In some embodiments of a compound of Formula (I), $R^1$ and $R^2$ are independently $C_1$-$C_6$ alkyl. In some embodiments of a compound of Formula (I), $R^1$ and $R^2$ are independently methyl, ethyl, propyl, isopropyl, or butyl. In some embodiments of a compound of Formula (I), $R^1$ and $R^2$ are independently methyl or ethyl. In some embodiments of a compound of Formula (I), $R^1$ and $R^2$ are methyl. In some embodiments of a compound of Formula (I), $R^1$ and $R^2$ are ethyl. In some embodiments of a compound of Formula (I), $R^1$ and $R^2$ are not hydrogen.

In some embodiments of a compound of Formula (I), $R^1$ and $R^2$ are independently $C_1$-$C_6$ hydroxyalkyl. In some embodiments of a compound of Formula (I), $R^1$ and $R^2$ are independently hydroxyethyl or propanediol. In some embodiments of a compound of Formula (I), $R^1$ and $R^2$ are hydroxyethyl. In some embodiments of a compound of Formula (I), $R^1$ and $R^2$ are 2-hydroxyethyl. In some embodiments of a compound of Formula (I), $R^1$ and $R^2$ are dihydroxypropyl. In some embodiments of a compound of Formula (I), $R^1$ and $R^2$ are 2,3-dihydroxypropyl.

In some embodiments of a compound of Formula (I), $R^1$ and $R^2$ are independently optionally substituted ($C_1$-$C_6$ alkyl)($C_3$-$C_8$ cycloalkyl). In some embodiments of a compound of Formula (I), $R^1$ and $R^2$ are independently substituted ($C_1$-$C_6$ alkyl)($C_3$-$C_8$ cycloalkyl). In some embodiments of a compound of Formula (I), $R^1$ and $R^2$ are 4-(hydroxymethyl)cyclohexyl)methyl.

In some embodiments of a compound of Formula (I), $R^1$ and $R^2$ are independently optionally substituted aryl. In some embodiments of a compound of Formula (I), $R^1$ and $R^2$ are phenyl.

In some embodiments of a compound of Formula (I), $R^1$ and $R^2$ are independently optionally substituted ($C_1$-$C_6$ alkyl)(aryl). In some embodiments of a compound of Formula (I), $R^1$ and $R^2$ are benzyl.

In some embodiments, the ester derivative contains less than about 10% impurity (w/w). In some embodiments, the ester derivative contains less than about 9% impurity (w/w). In some embodiments, the ester derivative contains less than about 8% impurity (w/w). In some embodiments, the ester derivative contains less than about 7% impurity (w/w). In some embodiments, the ester derivative contains less than about 6% impurity (w/w). In some embodiments, the ester derivative contains less than about 5% impurity (w/w). In some embodiments, the ester derivative contains less than about 4% impurity (w/w). In some embodiments, the ester derivative contains less than about 3% impurity (w/w). In some embodiments, the ester derivative contains less than about 2% impurity (w/w). In some embodiments, the ester derivative contains less than about 1% impurity (w/w). In some embodiments, the ester derivative contains less than about 0.5% impurity (w/w). In some embodiments, the ester derivative contains less than about 0.4% impurity (w/w). In some embodiments, the ester derivative contains less than about 0.3% impurity (w/w). In some embodiments, the ester derivative contains less than about 0.2% impurity (w/w). In some embodiments, the ester derivative contains less than about 0.1% impurity (w/w).

In some embodiments, the ester derivative contains less than about 250 ppm of any metals, less than about 240 ppm of any metals, less than about 230 ppm of any metals, less than about 220 ppm of any metals, less than about 210 ppm of any metals, less than about 200 ppm of any metals, less than about 190 ppm of any metals, less than about 180 ppm of any metals, less than about 170 ppm of any metals, less than about 160 ppm of any metals, less than about 150 ppm of any metals, less than about 140 ppm of any metals, less than about 130 ppm of any metals, less than about 120 ppm of any metals, less than about 110 ppm of any metals, less than about 100 ppm of any metals, less than about 90 ppm of any metals, less than about 80 ppm of any metals, less than about 70 ppm of any metals, less than about 60 ppm of any metals, less than about 50 ppm of any metals, less than about 40 ppm of any metals, less than about 30 ppm of any metals, less than about 20 ppm of any metals, less than about 10 ppm of any metals, less than about 5 ppm of any metals, less than about 4 ppm of any metals, less than about 3 ppm of any metals, less than about 2 ppm of any metals, less than about 1 ppm of any metals, less than about 0.9 ppm of any metals, less than about 0.8 ppm of any metals, less than about 0.7 ppm of any metals, less than about 0.6 ppm of any metals, less than about 0.5 ppm of any metals, less than about 0.4 ppm of any metals, less than about 0.3 ppm of any metals, less than about 0.2 ppm of any metals, less than about 0.1 ppm of any metals, less than about 0.09 ppm of any metals, less than about 0.08 ppm of any metals, less than about 0.07 ppm of any metals, less than about 0.06 ppm of any metals, less than about 0.05 ppm of any metals, less than about 0.04 ppm of any metals, less than about 0.03 ppm of any metals, less than about 0.02 ppm of any metals, or less than about 0.01 ppm of any metals.

Alcoholic Solvent

Described herein is a process for the transformation of a polyester into an ester derivative; the process comprising admixing the polyester with a mixture comprising:

(a) a solvent for swelling the polyester;
(b) an alcoholic solvent; and
(c) a sub-stoichiometric amount of an alkoxide.

In some embodiments, the process described herein comprises an alcoholic solvent. In some embodiments, the alcoholic solvent is a linear alcohol, branched alcohol, cyclic alcohol, or any combinations thereof. In some embodiments, the alcoholic solvent is selected from methanol, ethanol, n-propanol, isopropanol, t-butanol, ethylene glycol, glycerol, cyclohexane-1,4-diyldimethanol, phenol, benzyl alcohol, and any combinations thereof.

In some embodiments, the alcoholic solvent is a linear $C_1$-$C_4$ alcohol. In some embodiments, the alcoholic solvent is methanol, ethanol, propanol, butanol, or a combination thereof. In some embodiments, the alcoholic solvent is methanol, ethanol, propanol, or a combination thereof. In some embodiments, the alcoholic solvent is methanol. In some embodiments, the alcohol is ethanol. In some embodiments, the alcoholic solvent is a branched $C_3$-$C_4$ alcohol. In some embodiments, the alcoholic solvent is t-butanol, s-butanol, i-butanol, propanol, or any combinations thereof. In some embodiments, the alcoholic solvent is a cyclic $C_3$-$C_8$ alcohol. In some embodiments, the alcoholic solvent is cyclopropanol, cyclobutanol, cyclopentanol, cyclohexanol, cycloheptanol, cyclohexane-1,4-diyldimethanol, or any combinations thereof. In some embodiments, the alcoholic solvent is cyclohexane-1,4-diyldimethanol.

In some embodiments, the alcoholic solvent is a polyol. In some embodiments, the alcoholic solvent is selected from ethylene glycol, glycerol, and any combinations thereof.

In some embodiments, the alcoholic solvent is selected from phenol, benzyl alcohol, and any combinations thereof.

Solvent for Swelling the Polyester

Described herein is a process for the transformation of a polyester into an ester derivative; the process comprising admixing the polyester with a mixture comprising:

(a) a solvent for swelling the polyester;
(b) an alcoholic solvent; and
(c) a sub-stoichiometric amount of an alkoxide.

In some embodiments, the process described herein comprises pre-treating the polyester with a solvent for swelling the polyester prior to the addition of the alcoholic solvent and alkoxide. In some embodiments, the pre-treatment with the solvent for swelling the polyester is done for between about 5 mins and about 60 mins prior to the addition of the alcoholic solvent and alkoxide. In some embodiments, the pre-treatment with the solvent for swelling the polyester is done for between about 5 mins and about 40 mins prior to the addition of the alcoholic solvent and alkoxide. In some embodiments, the pre-treatment with the solvent for swelling the polyester is done for between about 5 mins and about 20 mins prior to the addition of the alcoholic solvent and alkoxide. In some embodiments, the pre-treatment with the solvent for swelling the polyester is done for between about 5 mins and about 10 mins prior to the addition of the alcoholic solvent and alkoxide. In some embodiments, the pre-treatment with the solvent for swelling the polyester is done for about 5 mins. In some embodiments, the pre-treatment with the solvent for swelling the polyester is done for about 10 mins. In some embodiments, the pre-treatment with the solvent for swelling the polyester is done for about 15 mins. In some embodiments, the pre-treatment with the solvent for swelling the polyester is done for about 20 mins. In some embodiments, the pre-treatment with the solvent for swelling the polyester is done for about 25 mins. In some embodiments, the pre-treatment with the solvent for swelling the polyester is done for about 30 mins. In some embodiments, the pre-treatment with the solvent for swelling the polyester is done for about 35 mins. In some embodiments, the pre-treatment with the solvent for swelling the polyester is done for about 40 mins. In some embodiments, the pre-treatment with the solvent for swelling the polyester is done for about 45 mins. In some embodiments, the pre-treatment with the solvent for swelling the polyester is done for about 50 mins. In some embodiments, the pre-treatment with the solvent for swelling the polyester is done for about 55 mins. In some embodiments, the pre-treatment with the solvent for swelling the polyester is done for about 60 mins.

In some embodiments, the process described herein comprises treating the polyester with a solvent for swelling the polyester at the same time as the addition of the alcoholic solvent and alkoxide.

In some embodiments, the solvent for swelling the polyester is selected from a non polar solvent, a polar aprotic solvent, a polar protic solvent, and any combinations thereof.

In some embodiments, the solvent for swelling the polyester is selected from dimethyl sulfoxide (DMSO), N,N-dimethylformamide (DMF), acetone, a halogenated solvent, n-hexane, nitrobenzene, methanol, benzyl alcohol, benzaldehyde, and any combinations thereof. In some embodiments, the solvent for swelling the polyester is selected from DMSO, a halogenated solvent, and any combinations thereof. In some embodiments, the solvent for swelling the polyester is DMSO. In some embodiments, the solvent for swelling the polyester is a halogenated solvent. In some embodiments, the solvent for swelling the polyester is a chlorinated solvent. In some embodiments, the solvent for swelling the polyester is dichloromethane, dichloroethane, tetrachloroethane, chloroform, tetrachloromethane, trichloroethane, or any combinations thereof. In some embodiments, the solvent for swelling the polyester is dichloromethane. In some embodiments, the solvent for swelling the polyester is methanol.

In some embodiments, the ratio of solvent for swelling the polyester to alcoholic solvent is between about 0.1:1 and about 2:1 (w:w). In some embodiments, the ratio of solvent for swelling the polyester to alcoholic solvent is between about 1:1 and about 2:1 (w:w). In some embodiments, the ratio of solvent for swelling the polyester to alcoholic solvent is between about 0.1:1 and about 2:1 (w:w), or between about 0.2:1 and about 2:1 (w:w), or between about 0.3:1 and about 2:1 (w:w), or between about 0.4:1 and about 2:1 (w:w), or between about 0.5:1 and about 2:1 (w:w), or between about 0.6:1 and about 2:1 (w:w), or between about 0.7:1 and about 2:1 (w:w), or between about 0.8:1 and about 2:1 (w:w), or between about 0.9:1 and about 2:1 (w:w), or between about 1:1 and about 2:1 (w:w), or between about 1:2 and about 2:1 (w:w), or between about 1:3 and about 2:1 (w:w), or between about 1:4 and about 2:1 (w:w), or between about 1:4 and about 2:1 (w:w), or between about 1:6 and about 2:1 (w:w), or between about 1:7 and about 2:1 (w:w), or between about 1:8 and about 2:1 (w:w), or between about 1:9 and about 2:1 (w:w), or between about 0.5:1 and about 1.5:1 (w:w), or between about 0.8:1 and about 1.2:1 (w:w), or between about 0.5:1 and about 1:1 (w:w), or between about 1:1 and about 1.5:1 (w:w). In some embodiments, the ratio of solvent for swelling the polyester to alcoholic solvent is between about 0.5:1 and about 1:1 (w:w).

Alkoxides

Described herein is a process for the transformation of a polyester into an ester derivative; the process comprising admixing the polyester with a mixture comprising:
(a) a solvent for swelling the polyester;
(b) an alcoholic solvent; and
(c) a sub-stoichiometric amount of an alkoxide.

In some embodiments, the process described herein comprises adding a sub-stoichiometric amount of an alkoxide. In some embodiments, the process described herein comprises adding a catalytic amount of an alkoxide.

"Sub-stoichiometric amount", as used herein, is used to indicate that the amount of material used is less than a stoichiometric amount. The term is used herein interchangeably with "catalytic amount." In some embodiments, a sub-stoichiometric amount is less than or equal to about 95% of a stoichiometric amount. In some embodiments, a sub-stoichiometric amount is less than or equal to about 90% of a stoichiometric amount. In some embodiments, a sub-stoichiometric amount is less than or equal to about 85% of a stoichiometric amount. In some embodiments, a sub-stoichiometric amount is less than or equal to about 80% of a stoichiometric amount. In some embodiments, a sub-stoichiometric amount is less than or equal to about 75% of a stoichiometric amount. In some embodiments, a sub-stoichiometric amount is less than or equal to about 70% of a stoichiometric amount. In some embodiments, a sub-stoichiometric amount is less than or equal to about 65% of a stoichiometric amount. In some embodiments, a sub-stoichiometric amount is less than or equal to about 60% of a stoichiometric amount. In some embodiments, a sub-stoichiometric amount is less than or equal to about 55% of a stoichiometric amount. In some embodiments, a sub-stoichiometric amount is less than or equal to about 50% of a stoichiometric amount. In some embodiments, a sub-stoichiometric amount is less than or equal to about 45% of a stoichiometric amount. In some embodiments, a sub-stoichiometric amount is less than or equal to about 40% of a stoichiometric amount. In some embodiments, a sub-stoichiometric amount is less than or equal to about 35% of a stoichiometric amount. In some embodiments, a sub-stoichiometric amount is less than or equal to about 30% of a stoichiometric amount. In some embodiments, a sub-stoichiometric amount is less than or equal to about 25% of a stoichiometric amount. In some embodiments, a sub-stoichiometric amount is less than or equal to about 20% of a stoichiometric amount. In some embodiments, a sub-stoichiometric amount is less than or equal to about 15% of a stoichiometric amount. In some embodiments, a sub-stoichiometric amount is less than or equal to about 10% of a stoichiometric amount.

"Stoichiometric amount", as used herein, is used to indicate that the amount of material used is equivalent to the number of ester linkages present in the polyester.

In some embodiments, the alkoxide, which comprises an alkoxide anion and a cation is selected from an alkali metal alkoxide, an alkaline earth metal alkoxide, a metal alkoxide, an ammonium alkoxide, and any combinations thereof. In some embodiments, the alkoxide anion is a $C_1$-$C_4$ alkoxide anion. In some embodiments, the alkoxide anion is selected from methoxide, ethoxide, n-propoxide, n-butoxide, t-butoxide, sec-butoxide, iso-butoxide, iso-propoxide, and a combination thereof. In some embodiments, the alkoxide anion is methoxide, ethoxide, or any combinations thereof. In some embodiments, the alkoxide anion is methoxide. In some embodiments, the cation is lithium, sodium, potassium, magnesium, calcium, strontium, barium, zinc, aluminum, or ammonium. In some embodiments, the alkoxide is sodium methoxide, potassium ethoxide, or aluminium tri-n-propoxide. In some embodiments, the ammonium alkoxide is a tetraalkylammonium alkoxide. In some embodiments, the ammonium alkoxide is a tetrabutylammonium alkoxide. In some embodiments, the alkoxide is sodium methoxide, potassium ethoxide, aluminium tri-n-propoxide, or tetrabutylammonium methoxide.

In some embodiments, the alkoxide is generated in-situ by addition of an alkali metal, an alkaline earth metal, or a metal to the alcoholic solvent.

In some embodiments, the ratio of polyester to alkoxide is between about 15:1 and about 125:1 (w:w), or between about 15:1 and about 100:1 (w:w), or between about 15:1 and about 80:1 (w:w), or between about 15:1 and about 60:1 (w:w), or between about 15:1 and about 40:1 (w:w), or between about 15:1 and about 25:1 (w:w), or between about 15:1 and about 20:1 (w:w), or between about 20:1 and about 25:1 (w:w), or between about 20:1 and about 50:1 (w:w), or between about 30:1 and about 60:1 (w:w), or between about 40:1 and about 70:1 (w:w), or between about 50:1 and about 80:1 (w:w), or between about 60:1 and about 90:1 (w:w), or between about 20:1 and about 125:1 (w:w), or between about 40:1 and about 125:1 (w:w), or between about 60:1 and about 125:1 (w:w), or between about 80:1 and about 125:1 (w:w), or between about 100:1 and about 125:1 (w:w). In some embodiments, the ratio of polyester to alkoxide is between about 20:1 and about 25:1 (w:w).

Reaction Time

Described herein is a process for the transformation of a polyester into an ester derivative; the process comprising admixing the polyester with a mixture comprising:
(a) a solvent for swelling the polyester;
(b) an alcoholic solvent; and
(c) a sub-stoichiometric amount of an alkoxide.

In some embodiments, the admixing of the polyester with the solvent for swelling the polyester, the alkoxide, and the alcoholic solvent is performed for a sufficient time. In some embodiments, the admixing of the polyester with the solvent for swelling the polyester, the alkoxide, and the alcoholic solvent is performed until an about 70% yield of desired ester is achieved. In some embodiments, the admixing of the polyester with the solvent for swelling the polyester, the alkoxide, and the alcoholic solvent is performed until an about 75% yield of desired ester is achieved. In some embodiments, the admixing of the polyester with the solvent for swelling the polyester, the alkoxide, and the alcoholic solvent is performed until an about 80% yield of desired ester is achieved. In some embodiments, the admixing of the polyester with the solvent for swelling the polyester, the alkoxide, and the alcoholic solvent is performed until an about 85% yield of desired ester is achieved. In some embodiments, the admixing of the polyester with the solvent for swelling the polyester, the alkoxide, and the alcoholic solvent is performed until an about 90% yield of desired ester is achieved. In some embodiments, the admixing of the polyester with the solvent for swelling the polyester, the alkoxide, and the alcoholic solvent is performed until an about 95% yield of desired ester is achieved.

In some embodiments, the admixing of the polyester with the solvent for swelling the polyester, the alkoxide, and the alcoholic solvent is performed for between about 10 mins and 5 hrs, or between about 10 mins and 4 hrs, or between about 10 mins and 3 hrs, or between about 10 mins and 2 hrs, or between about 20 mins and 2 hrs, or between about 30 mins and 2 hrs, or between about 40 mins and 2 hrs, or between about 30 mins and 1 hr, or between about 30 mins and 1.5 hrs. In some embodiments, the admixing of the polyester with the solvent for swelling the polyester, the alkoxide, and the alcoholic solvent is performed for about 10 mins, or about 15 mins, or about 20 mins, or about 25 mins, or about 30 mins, or about 35 mins, or about 40 mins, or about 45 mins, or about 50 mins, or about 60 mins, or about 70 mins, or about 80 mins, or about 90 mins, or about 100 mins, or about 110 mins, or about 120 mins, or about 130 mins, or about 140 mins, or about 150 mins, or about 160 mins, or about 170 min, or about 180 mins. In some embodiments, the admixing of the polyester with the solvent for swelling the polyester, the alkoxide, and the alcoholic solvent is performed for about 1 hr, or about 2 hrs, or about 3 hrs, about 4 hrs, or about 5 hrs.

Temperature

Described herein is a process for the transformation of a polyester into an ester derivative; the process comprising admixing the polyester with a mixture comprising:
(a) a solvent for swelling the polyester;
(b) an alcoholic solvent; and
(c) a sub-stoichiometric amount of an alkoxide.

In some embodiments, the process disclosed herein is conducted at ambient temperature. In some embodiments, ambient temperature is 25±5° C.

In some embodiments, the process disclosed herein is conducted without external heat. In some embodiments, the process is exothermic and the temperature of the reaction mixture rises to at least 30° C., at least 35° C., at least 40° C., at least 45° C., at least 50° C., at least 55° C., or at least 60° C. In some embodiments, no external heat sources are used to increase the temperature of the reaction mixture.

In some embodiments, the process disclosed herein is conducted with external heat. In some embodiments, the process disclosed herein is conducted with external heat at between about 25° C. and about 80° C., or between about 25° C. and about 60° C., or between about 40° C. and about 60° C., or between about 40° C. and about 50° C., or between about 30° C. and about 50° C. In some embodiments, the process disclosed herein is conducted at about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., about 52° C., about 53° C., about 54° C., about 55° C., about 56° C., about 57° C., about 58° C., about 59° C., about 60° C., about 65° C., about 70° C., about 75° C., or about 80° C.

Pressure

In some embodiments, the process disclosed herein is conducted at atmospheric pressure. In some embodiments, the process disclosed herein is conducted at elevated pressures. In some embodiments, the process disclosed herein is conducted at a pressure between about atmospheric pressure and about 220 psi, or between about atmospheric pressure and about 200 psi, or between about atmospheric pressure and about 150 psi, or between about atmospheric pressure and about 100 psi, or between about atmospheric pressure and about 50 psi, or between about 20 and about 150 psi, or between about 50 and about 100 psi. In some embodiments, the process disclosed herein is conducted at about 14 psi, about 15 psi, about 16 psi, about 17 psi, about 18 psi, about 19 psi, about 20 psi, about 30 psi, about 40 psi, about 50 psi, about 60 psi, about 70 psi, about 80 psi, about 90 psi, about 100 psi, about 110 psi, about 120 psi, about 130 psi, about 140 psi, about 150 psi, about 160 psi, about 170 psi, about 180 psi, about 190 psi, about 200 psi, about 210 psi, or about 220 psi.

Agitation

Described herein is a process for the transformation of a polyester into an ester derivative; the process comprising admixing the polyester with a mixture comprising:
(a) a solvent for swelling the polyester;
(b) an alcoholic solvent; and
(c) a sub-stoichiometric amount of an alkoxide.

In some embodiments, the process disclosed herein is conducted without agitation. In some embodiments, the process disclosed herein is conducted with increased agitation. In some embodiments, a stirred batch reactor is used to provide agitation. In some embodiments, a continuous reactor is used to provide agitation.

Certain Terminology

The section headings used herein are for organizational purposes only and are not to be construed as limiting the subject matter described.

Unless defined otherwise, all technical and scientific terms used herein have the same meaning as is commonly understood to which the claimed subject matter belongs. In the event that there are a plurality of definitions for terms herein, those in this section prevail.

It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the term "about" or "approximately" means within 10%, preferably within 10%, and more preferably within 5% of a given value or range.

As used herein, ambient temperature is a colloquial expression for the typical or preferred indoor (climate-controlled) temperature to which people are generally accustomed. It represents the small range of temperatures at which the air feels neither hot nor cold, approximately 21° C. In some embodiments, ambient temperature is 25±5° C. In some embodiments, ambient temperature is 18° C. In some embodiments, ambient temperature is 19° C. In some embodiments, ambient temperature is 20° C. In some embodiments, ambient temperature is 21° C. In some embodiments, ambient temperature is 22° C. In some embodiments, ambient temperature is 23° C. In some embodiments, ambient temperature is 24° C. In some embodiments, ambient temperature is 25° C. In some embodiments, ambient temperature is 26° C. In some embodiments, ambient temperature is 27° C. In some embodiments, ambient temperature is 28° C. In some embodiments, ambient temperature is 29° C. In some embodiments, ambient temperature is 30° C.

As used in this specification and the appended claims, depolymerization, refer to a way of breaking down a polymer to its starting material. It is essentially the opposite of polymerization. In some embodiments, the depolymerization is achieved by glycolysis, methanolysis or hydrolysis, categorized by the depolymerization reactant used, such as glycol, methanol or water, respectively.

Definition of standard chemistry terms may be found in reference works, including but not limited to, Carey and Sundberg "Advanced Organic Chemistry 4$^{th}$ Ed." Vols. A (2000) and B (2001), Plenum Press, New York.

The terms below, as used herein, have the following meanings, unless indicated otherwise:

"Alkyl" refers to a straight or branched hydrocarbon chain radical which is attached to the rest of the molecule by a single bond. A linear alkyl comprising up to 4 carbon atoms is referred to as a linear $C_1$-$C_4$ alkyl, likewise, for example, a linear alkyl comprising up to 3 carbon atoms is a linear $C_1$-$C_3$ alkyl. Linear alkyl groups include linear $C_1$-$C_4$ alkyl, linear $C_1$-$C_3$ alkyl, linear $C_1$-$C_2$ alkyl, linear $C_2$-$C_3$ alkyl and linear $C_2$-$C_4$ alkyl. Representative alkyl groups include, methyl, ethyl, propyl, and butyl. A branched alkyl comprising between 3 and 4 carbon atoms is referred to as a branched $C_3$-$C_4$ alkyl. Representative branched alkyl groups include, but are not limited to t-butyl, sec-butyl, isobutyl, and isopropyl. Unless stated otherwise specifically in the specification, an alkyl is optionally substituted with oxo, halogen, —CN, —CF$_3$, —OH, —OMe, —NH$_2$, or —NO$_2$. In some embodiments, an alkyl is optionally substituted with oxo, halogen, —CN, —CF$_3$, —OH, or —OMe. In some embodiments, the alkyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo atoms, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Hydroxyalkyl" refers to an alkyl radical, as defined above, that is substituted by one or more —OH groups, e.g., hydroxymethyl, hydroxyethyl, hydroxypropyl, propanediol, and the like.

"Cycloalkyl" refers to a stable, partially or fully saturated, monocyclic or polycyclic carbocyclic ring, which may include fused or bridged ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[3.3.0]octane, bicyclo[4.3.0]nonane, cis-decalin, trans-decalin, bicyclo[2.1.1] hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused or bridged ring systems. In some embodiments, the aryl is a 6- to 10-membered aryl. In some embodiments, the aryl is a 6-membered aryl. Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. In some embodiments, the aryl is phenyl. Unless stated otherwise specifically in the specification, an aryl may be optionally substituted, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, an aryl is optionally substituted with halogen, methyl, ethyl, —CN, —CF$_3$, —OH, —OMe, —NH$_2$, or —NO$_2$. In some embodiments, an aryl is optionally substituted with halogen, methyl, ethyl, —CN, —CF$_3$, —OH, or —OMe. In some embodiments, the aryl is optionally substituted with halogen.

EXAMPLES

The following examples are intended to illustrate but not limit the disclosed embodiments.

Example 1

Polyethylene terephthalate (1000 g) was introduced in a reactor. Dichloromethane (500 g) was added and the mixture was stirred at room temperature and at atmospheric pressure for about 40 mins. Sodium methoxide and methanol were then added to the reaction mixture was stirred and heated for 120 mins (see table below for amounts, time, and temperature details).

The reaction mixture was then filtered and the filter cake was washed with methanol. The filter cake was then melted and filtered at 140° C. to remove any unreacted materials. The filtered dimethyl terephthalate was then distilled under vacuum at 200° C. The liquid recovered from the filtration was distilled to recover the solvents and the mono ethylene glycol.

|  | Weight of methanol (g) | Weight of sodium methoxide (g) | Reaction time (min) | Reaction temperature (° C.) | Yield (%) |
| --- | --- | --- | --- | --- | --- |
| Example 1A | 667 | 32 | 120 | 55 | 90 |
| Example 1B | 600 | 54 | 120 | 50 | 90 |
| Example 1C | 580 | 50 | 120 | 60 | 90 |

Example 2

Polyethylene terephthalate (1000 g) was introduced in a reactor. DMSO (500 g) was added and the mixture was stirred at room temperature and at atmospheric pressure for about 40 mins. Sodium methoxide (45 g) and methanol (550 g) were then added to the reaction mixture was stirred and heated at 55° C. for 120 mins.

The reaction mixture was then filtered and the filter cake was washed with methanol. The filter cake was then melted and filtered at 140° C. to remove any unreacted materials. The filtered dimethyl terephthalate was then distilled under vacuum at 200° C. The liquid recovered from the filtration was distilled to recover the solvents and the mono ethylene glycol.

Dimethyl terephthalate was obtained in 89% yield.

What is claimed is:

1. A process for the transformation of a polyester selected from polyethylene terephthalate and poly(ethylene glycol-co-1,4-cyclohexanedimethanol terephthalate) into dimethyl terephthalate; the process comprising admixing the polyester with a mixture comprising:
   (a) methanol; and
   (b) a sub-stoichiometric amount of an alkoxide;
   wherein the process is performed at a temperature between about 25° C. and about 80° C.;
   wherein the ratio of the polyester to the alkoxide is between about 20:1 and about 50:1 (w:w); and wherein the process achieves at least about 70% yield of dimethyl terephthalate.

2. The process of claim 1, wherein the alkoxide is selected from an alkali metal alkoxide, an alkaline earth metal alkoxide, a metal alkoxide, an ammonium alkoxide and any combinations thereof.

3. The process of claim 1, wherein the alkoxide is selected from sodium methoxide, potassium ethoxide, aluminium tri-n-propoxide, and tetrabutylammonium methoxide.

4. The process of claim 1, wherein the alkoxide is sodium methoxide.

5. The process of claim 1, wherein the alkoxide is generated in-situ by addition of an alkali metal, an alkaline earth metal, or a metal to the methanol.

6. The process of claim 1, wherein the ratio of the polyester to the alkoxide is between about 20:1 and about 25:1 (w:w).

7. The process of claim 1, wherein the process achieves at least about 80% yield of dimethyl terephthalate.

8. The process of claim 1, wherein the process achieves at least about 90% yield of dimethyl terephthalate.

9. The process of claim 1, wherein the process achieves at least about 95% yield of dimethyl terephthalate.

10. The process of claim 1, wherein the process is performed at atmospheric pressure.

* * * * *